United States Patent
Groke et al.

(10) Patent No.: US 6,407,030 B1
(45) Date of Patent: Jun. 18, 2002

(54) METHOD FOR PRODUCING CATALYSTS FOR SYNTHESIZING MALEIC ANHYDRIDE BY MEANS OF GAS PHASE OXIDATION

(75) Inventors: Dirk Groke, Taufkirchen; Richard Bosch, Germering; Joachim Lotz; Hans-Jürgen Eberle, both of München, all of (DE)

(73) Assignee: Consortium für elektrochemische Industrie GmbH, Munich (DE)

( * ) Notice: Subject to any disclaimer, the term of this patent is extended or adjusted under 35 U.S.C. 154(b) by 0 days.

(21) Appl. No.: 09/786,375

(22) PCT Filed: Aug. 26, 1999

(86) PCT No.: PCT/EP99/06274

§ 371 (c)(1),
(2), (4) Date: Jun. 1, 2001

(87) PCT Pub. No.: WO00/13793

PCT Pub. Date: Mar. 16, 2000

(30) Foreign Application Priority Data

Sep. 3, 1998 (DE) .......................................... 198 40 224

(51) Int. Cl.⁷ .......................... B01J 27/198; B01J 27/19; B01J 23/00; B01J 27/192; B01J 27/185

(52) U.S. Cl. ...................... 502/209; 502/210; 502/211; 502/212; 502/213; 502/306; 502/311; 502/312; 502/313; 502/314; 502/315; 502/316

(58) Field of Search ................ 502/209–213, 502/306, 311–316

(56) References Cited

U.S. PATENT DOCUMENTS

| | | | | |
|---|---|---|---|---|
| 4,043,943 A | * | 8/1977 | Schneider | 252/437 |
| 4,132,670 A | | 1/1979 | Katsumoto et al. | 252/437 |
| 4,158,671 A | * | 6/1979 | Barone | 260/546 |
| 4,251,390 A | | 2/1981 | Barone | 252/435 |
| 4,337,174 A | * | 6/1982 | Mount et al. | 252/437 |
| 4,382,876 A | | 5/1983 | Neubold et al. | 252/435 |
| 4,569,925 A | * | 2/1986 | Yang et al. | 502/209 |
| 4,784,981 A | * | 11/1988 | Alpers et al. | 502/209 |
| 5,155,235 A | * | 10/1992 | Takashi et al. | 549/262 |
| 5,185,455 A | | 2/1993 | Ebner | 549/259 |
| 5,288,880 A | | 2/1994 | Matsuura | 549/260 |
| 5,530,144 A | * | 6/1996 | Tsurita et al. | 549/259 |
| 6,048,987 A | * | 4/2000 | Groke et al. | 549/260 |

FOREIGN PATENT DOCUMENTS

| | | |
|---|---|---|
| DE | 2700635 | 7/1978 |
| DE | 3010710 | 9/1981 |
| DE | 3018849 | 7/1991 |
| EP | 0072381 | 3/1985 |
| EP | 0151912 | 8/1988 |
| EP | 0458541 | 11/1995 |
| WO | 93/01155 | 1/1993 |
| WO | 95/29006 | 11/1995 |
| WO | 96/25230 | 8/1996 |

OTHER PUBLICATIONS

English Derwent Abstract AN 1977–32852Y [19] Corresponding to DE 27 00 635 (Jan. 1977).
English Derwent Abstract AN 1981–72009D [40] Corresponding to DE 30 10 710 (Mar. 1980).
Doi. T., Miyalee; T.; Applied Catal. A. General 164 (1997), 141–148 (Apr. 1977).

* cited by examiner

*Primary Examiner*—Mark L. Bell
*Assistant Examiner*—Patricia L. Hailey
(74) *Attorney, Agent, or Firm*—Collard & Roe, P.C.

(57) ABSTRACT

A method is provided for producing catalysts useful for synthesizing maleic anhydride by oxidizing saturated and/or unsaturated $C_4$ hydrocarbons. A vanadium (V) compound is reacted with a mixture of phosphorous and phosphoric acids in a particular ratio, in a solvent mixture containing a structure former, and an entrainer and where the water of reaction together with entrainer is distilled off and the resulting precursor is subjected to calcination.

10 Claims, No Drawings

METHOD FOR PRODUCING CATALYSTS FOR SYNTHESIZING MALEIC ANHYDRIDE BY MEANS OF GAS PHASE OXIDATION

CROSS REFERENCE TO RELATED APPLICATIONS

Applicants claim priority under 35 U.S.C. §119 of German Application No. 198 40 224.4 filed Sep. 3, 1998. Applicants also claim priority under 35 U.S.C. §120 of PCT/EP99/06274 filed Aug. 26, 1999. The international application under PCT article 21(2) was not published in English.

BACKGROUND OF THE INVENTION

1) Field of the Invention

The invention relates to a process for preparing catalysts for the partial gas-phase oxidation of saturated and/or unsaturated $C_4$-hydrocarbons to form maleic anhydride (MA).

2) Background Art

The preparation of maleic anhydride from $C_4$-hydrocarbons has been known for more than 20 years. It is carried out using catalysts based on vanadyl phosphates (vanadyl pyrophosphate, vanadium-phosphorous oxides). These vanadyl phosphates are prepared via a catalyst precursor which can be prepared in aqueous or organic medium. The precursor is then, in a second step before or after shaping, converted either in the reactor (in situ) or externally into the actual catalytic reactive substance.

The reaction of the $C_4$-hydrocarbon over the catalyst is carried out in various types of reactor. Reactors used are fixed-bed, fluidized-bed and also riser reactors; in the case of fixed-bed reactors, use is made exclusively of catalysts based on vanadyl phosphates in the form of unsupported catalysts. EP-B 72381 and WO-A 96/25230 disclose the use of coated catalysts too.

The precursor can be prepared either in an aqueous medium or in an organic medium. In industry, preference is given to carrying out the preparation in an organic solvent. Here, isobutanol (2-methylpropan-1-ol) has proven useful as solvent or reaction medium. Compared with the catalysts prepared in an organic medium, those prepared in an aqueous medium have significantly lower activity and selectivity. A cause of the difference is the lower specific surface area of the catalysts prepared by the aqueous route. Furthermore, the use of an organic solvent brings process engineering advantages, namely the precursor formed is easier to separate from the reaction mixture since the product is insoluble in the solvent. The solvent has to meet a number of prerequisites. Thus, for example, it must not react with the phosphorous compounds required for formation of the vanadyl phosphate. In addition, its boiling point has to be within a range in which the formation of the desired vanadyl phosphates is observed. As is generally known, the reaction temperature strongly influences the rate of catalyst formation. Since the reaction is usually carried out in the boiling solvent, the boiling point of the solvent plays an important role. The solvent also has a strong influence on the morphology of the reaction product and sometimes even on the phases formed (Doi, T.; Miyake, T.; Applied Catal. A. General 164 (1997), 141–148).

The vanadium-containing starting compound used is generally vanadium pentoxide. Phosphoric acid generally serves as phosphorous compound. Since the vanadium is present in the oxidation state IV in the target compound, a reduction by means of a suitable reducing agent is necessary. Many compounds have been described for this purpose. Thus, use is made of, for example, gaseous HCl, oxalic acid, benzyl alcohol, isobutanol, hydrazine and also many other reducing agents. The nature of the reducing agent plays a minor role in the reaction.

U.S. Pat. No. 4,132,670 describes a process for preparing vanadyl phosphate catalysts. In this process, vanadium pentoxide is reacted in an alcohol, preferably isobutanol, to give a vanadium(IV) compound. The reaction of vanadium(V) to vanadium(IV) is effected by the solvent used. Subsequently, the vanadium phosphate precursor is prepared using concentrated $H_3PO_4$. The water content of the reaction mixture in the preparation of the precursor is here described as an important parameter and a low water content in the reaction mixture is recommended.

U.S. Pat. No. 4,382,876 discloses a process for preparing catalysts in which a vanadium(V) compound and isobutanol as solvent are placed in a reaction vessel and $H_3PO_3$ as reducing agent is added in relatively small amounts. The reduction of the vanadium(V) compound to vanadium(IV) in that invention occurs by means of a combined reduction by the tertiary alcohol and the phosphorous acid. The water formed in this process together with the solvent are distilled off batchwise a number of times. This procedure has the disadvantage that further water is continuously formed in the reaction mixture and this is only distilled off after a certain time. Thus, a continually low water content is not possible, which leads to a poorer performance of the future catalyst.

WO-A 95/29006 likewise discloses a process for preparing vanadyl phosphate catalysts. Here too, a vanadium(V) compound is reacted with phosphoric acid in isobutanol. In. this process, the water content is controlled by addition of highly concentrated phosphoric acid to the reaction mixture in order to absorb the water of reaction formed. The total water content of the reaction mixture is here determined by the phosphorous compounds used (85% $H_3PO_4$, 100% $H_3PO_4$, 106% $H_3PO_4$ or polyphosphoric acids) and by the water formed in the reaction (by the reduction of vanadium (V) to vanadium(IV) compounds). Major-disadvantages of this process are the high costs and the difficulty of handling concentrated phosphoric acid and polyphosphoric acid.

The reaction of the starting substances to form the desired vanadyl phosphate can in principle be carried out in various ways:

1. reduction of the vanadium(V) compound to vanadium (IV), subsequent reaction with the phosphorous compound to give vanadyl(IV) phosphate,
2. reaction of the vanadium(V) compound with the phosphorous compound to form the corresponding vanadium(V) phosphate and subsequent reduction to vanadyl(IV) phosphate, or
3. parallel reduction and reaction with the phosphorous compound to give vanadyl(IV) phosphate.

After the reaction is complete, the suspended or dissolved vanadyl phosphate is separated from the reaction mixture by suitable methods, for example filtration or evaporation, dried and converted into the active catalyst in a further step, namely calcination or activation. Shaping for use in fixed-bed reactors is carried out either before or after calcination, for example by tableting or by extrusion. A further possible way of shaping the catalyst is the production of coated catalysts as are also used in other processes, for example the synthesis of phthalic anhydride from o-xylene or naphthalene.

The calcination of the precursor, i.e. the conversion into the actual catalyst, can be carried out either externally or in the reactor (in situ) in which the conversion of the $C_4$-hydrocarbons into maleic anhydride is carried out.

U.S. Pat. No. 4,382,876 discloses a process in which the precursor obtained in the first step is converted into the actual catalyst in a second step in the reactor itself. Here, the precursor is activated by heating at a rate of less than 1° C./min in order to avoid hot spots in the catalyst. This in-situ calcination is carried out in the presence of $C_4$-hydrocarbon and air and the precursor is heated to a temperature of from 450° C. to 510° C. After this temperature has been held for from about 12 to 72 hours, the calcined material is slowly cooled again.

A major disadvantage of this process is that the final activity of the catalyst is reached only after some hundreds of hours.

Apart from the calcination processes described, external activations are also known. WO-A 95/29006 describes a process for calcination in which the precursor is reacted in an atmosphere of air, water vapour and inert gas. Here, the precursor is slowly heated at a heating rate of less than 1° C./min in a number of steps to a temperature in the range from 350° C. to 550° C. This temperature is held for from 2 to 8 hours, giving a mean oxidation state of vanadium of less than +4.5. U.S. Pat. No. 5,185,455 discloses a similar process for external calcination. Here, the tabletted precursor is heated stepwise in a defined gas atmosphere to a temperature of 425° C. (first temperature ramp up to 250° C.) and held at this temperature for a period of 6 hours. The oxygen and water content of the calcination gas plays an important role in determining the future performance of the catalyst.

These processes have economic advantages since they do not occupy the reactor for a number of weeks at reduced yield until the catalyst has been completely activated, as is the case in in-situ calcination. In addition, the precursor can be activated in relatively small sub-batches in the external calcination, which allows continuous quality monitoring and the entire catalyst batch is therefore not subjected to the risk of loss. The external calcination enables the conditions required for optimum activation of the precursor to form the active catalyst, (e.g. oxygen content and temperature) to be set more uniformly and reliably. In contrast, the in-situ calcination in a fixed-bed reactor leads, for example, to nonuniform conversion of the catalyst across the reactor or along the length of the reactor tube.

The external calcination of the precursor is generally carried out in defined gas atmospheres (gas mixtures of oxygen, inert gas and water vapour) and using a precisely defined temperature programme. The catalyst formed using this procedure immediately has its full activity, in contrast to the catalyst calcined in situ. The oxygen content (control of the mean oxidation state of vanadium), the concentration of water in the furnace atmosphere and the parameters of the temperature programme (steepness of the temperature ramps, final temperatures and hold times) are important in influencing the performance of the catalysts obtained.

To control the catalytic properties of the catalysts, U.S. Pat. No. 4,132,670, EP-A 0458541, DE-A 3018849 (U.S. Pat. No. 4,251,390), WO-A 93/01155, U.S. Pat. No. 5,288, 880 have proposed the addition of many compounds as promoters or dopants in widely differing concentrations. Compounds used here are, for example, compounds of the elements Mo, Zn, Fe, Co, Li, Ce, Zr, U, Bi and Cr, with atom number ratios of vanadium:promoter element in the range from 1:0.2 to 1:0.001 being described. The promoter can be added at various points in time during the production process. Use has been made of techniques in which the addition is carried out during the reaction to form the precursor (homogeneous distribution of the promoter in the precursor) or else impregnation methods by means of which the previously synthesized precursor is surface-coated with the promoter.

To control the structure of the catalyst formed, EP-A 0151912 describes the use of surface-active, alcohol-modifying substances such as HI, $SO_2$ or fuming sulphuric acid.

Apart from the use of promoters, the mixing-in of inert materials to control the catalyst activity has also been described. Examples of inert additives are $SiO_2$, $TiO_2$ and silicon carbide. These materials are generally added after the synthesis of the precursor is complete and before the catalyst is shaped.

Furthermore, the use of additives which control the pore structure of the shaped catalyst used have also been described relatively recently. Here, for example, certain amounts of higher alkanoic acids are added to the dried precursor before shaping. In an additional process step, these substances are finally removed again from the shaped body after shaping, as a result of which a defined pore structure can be achieved.

The processes which have been described for preparing catalysts for the synthesis of maleic anhydride all have a number of disadvantages. Thus, for example, the reduction of vanadium(V) by means of hydrogen chloride gas results in increased corrosion within the plants. The resulting waste chlorine gases and chloride wastes have to be disposed of at considerable expense and sometimes contaminate the precursor. A further disadvantage is associated with the amounts of water formed as a result of the reaction. The methods described in the prior art for removing water from the reaction mixture either impair the performance of the future catalyst or can only be carried out with difficulty and at high cost, for example when using polyphosphoric acid.

It is therefore an object of the invention to develop a process for preparing catalysts for the synthesis of maleic anhydride by gas-phase oxidation, which process avoids the abovementioned disadvantages.

SUMMARY OF THE INVENTION

The invention provides a process for preparing catalysts based on vanadyl phosphates for the synthesis of maleic anhydride by oxidation of saturated and/or unsaturated $C_4$-hydrocarbons by reacting a vanadium(V) compound with a mixture of phosphorous and phosphoric acids in a solvent mixture, characterized in that the molar $H_3PO_3/H_3PO_4$ ratio is from 1:1 to 1:2.5, the solvent used is a mixture of isobutanol, a structure former selected from the group consisting of mono-functional and polyfunctional alcohols, monofunctional and polyfunctional amines, organic phosphates, phosphites and phosphonates, and an entrainer selected from the group consisting of alkylaromatics and cycloalkanes, where the molar ratio of vanadium to structure former is in the range from 10:1 to 100:1, and the water of reaction together with entrainer is continuously removed at the boiling point, where the residual water content of the runback and the resulting residual water content of the reaction mixture is less than 0.5% by volume, and the precursor obtained in this way is subsequently subjected to a calcination in which a temperature programme comprising 3 ramps is employed, where the ramps are as follows:

ramp 1: initial temperature: $\leq 50°$ C., heating rate: from 5 to 20° C./min, final temperature: from 100 to 250° C., hold time: from 0 to 3 h, ramp 2: initial temperature=final temperature of ramp 1, heating rate: from 1 to 10° C./min, final temperature: from 150 to 300° C., hold time: from 0 to 3 h, ramp 3: initial temperature=final temperature of ramp 2, heating rate: from 0.1 to 3° C./min, final temperature: from 380 to 460° C., hold time: from 2 to 8 h, and gas mixtures of air, inert gas and water vapour in a volume ratio of 0.1–0.5:0.1–0.5:0.0–0.8 are used during these temperature ramps.

DESCRIPTION OF THE PREFERRED EMBODIMENTS

A vanadium(V) compound is suspended in a mixture of an agent which influences the structure of the vanadyl phosphate, for example benzyl alcohol or isobutanol, and an auxiliary which makes it possible to remove the water formed and/or introduced (known as an "entrainer"). The suspension is heated and, after reaching the boiling point, a mixture of phosphorous acid and phosphoric acid is added. As vanadium(V) compound, preference is given to using vanadium pentoxide. Other vanadium(V) compounds, for example its oxychlorides, can also be used.

As phosphorus components, use is made of phosphorous acid and phosphoric acid. The phosphorous acid serves both as reducing agent for the vanadium(V) and as a source of phosphorus. The use of a further reducing agent can therefore be dispensed with. The phosphorous acid is preferably used in solid form for preparing the mixture, but can also be used as a solution. Preference is given to a phosphorous acid having a purity/strength of from 85 to 100% by weight, particularly preferably 85% by weight. The phosphoric acid mixture is prepared by dissolving the phosphorous acid in the phosphoric acid, if appropriate with gentle heating. The mixture of $H_3PO_3/H_3PO_4$ has a molar mixing ratio of from 1:1 to 1:2.5, preferably from 1:1.5 to 1:2.0.

The vanadium compound and the phosphorus compounds are used in such amounts that the atom number ratio of vanadium:phosphorus is in the range from 1:0.9 to 1:2.0. The vanadium-phosphorus compound obtained in this way has a mean vanadium oxidation state of from 3.85 to 4.3, with the molar vanadium:phosphorus ratio in the isolated compound being in the range from 1:0.9 to 1:1.1.

The mixture of phosphorous acid and phosphoric acid is added immediately after the boiling point of the vanadium pentoxide/solvent suspension has been reached. A "prereduction period" as is described in other patents is not employed.

After the addition of the phosphorus component is complete, the reaction mixture is held under reflux conditions for a period of from 4 to 24 hours, preferably from 12 to 20 hours.

The solvent in which the reaction is carried out is isobutanol (2-methylpropan-1-ol). However, it is also possible to employ other inert solvents having a boiling point of about 100° C., for example toluene. An important aspect of the process claimed is that only a small amount of a structure-modifying agent has to be added.

As structure modifier, it is possible to use the following classes of compound: monofunctional and polyfunctional alcohols, for example ethanediol, 1,3-propanediol, n-hexanol, diphenylmethanol, preferably benzyl alcohol and alpha-omega-alkanediols, monofunctional and polyfunctional amines, for example n-propylamine, isobutylamine, ethylenediamine, preferably n-decylamine and propylenediamine, organic phosphates, for example butyl phosphate, dibutyl phosphate, trimethyl phosphate, preferably tributyl phosphate, phosphites or phosphonates, for example methylphosphonic acid, trimethyl phosphite, dibutylphosphonic acid, preferably tributyl phosphite, or mixtures thereof. owing to their chemical structure, these compounds can be incorporated (intercalated) in the layer structure of the precursor and thus influence the morphology of the material, i.e. the type and number of defects formed. The molar ratio of structure modifier to vanadium used is from 0.1% to 10%. The small amount required clearly distinguishes the process described here from other methods of preparation in which the additions, in particular the addition of benzyl alcohol, are made in a molar ratio of vanadium : additive of from 1:0.5 to 1:1.0. These added substances there serve as reducing agent; a structure-modifying effect when using small amount is not described (EP-A 0151912).

In addition, "entrainers" are added to the reaction mixture. These make it possible to remove water formed during the reaction from the reaction mixture. A number of substances can be used as entrainers. In general, use is made of nonpolar compounds which are only slightly miscible with water, for example alkylaromatics and cycloalkanes. Owing to their ready availability, preference is given to using toluene, xylenes, cyclohexane and benzene. Cyclohexane is particularly preferred as entrainer. The amount added to the isobutanol lies in a range from 5 to 15% by volume, preferably from 8 to 12% by volume, of the amount of solvent used.

While the reaction mixture is boiling, the ternary mixture of solvent, entrainer and water of reaction formed is continuously taken from the reactor via an external circuit. Within this circuit, the ternary azeotrope is conveyed into a vessel which allows the separation of the 2-phase condensate and thus the removal of the water-rich phase. The mixture of solvent and entrainer which has been depleted in water is recirculated to the reactor. After the separation, the residual water content of the recirculated mixture is less than 0.5% by volume. This procedure ensures that the water content of the reaction mixture is always kept below 0.5% by volume. This is an important criterion in respect of the selectivity and conversion of the finished catalyst.

In the preparation according to the invention of the precursor, doping of the catalyst may, if desired, also be carried out. Doping of the catalyst can be carried out in various ways. One method is to add metal compounds in the form of soluble compounds of the elements Mo, Wo, Bi, Cr, Co, Ni, Fe, Li, Ce, Zr, U and Zn, preferably Mo, Cr, Bi, Co, Zn, Li and Ce, to the organic solvent mixture in an atom number ratio of vanadium:doping element of from 1:0.1 to 1:0.001. A further way is to dope the catalyst precursor formed after the. reaction is complete and immediately before drying or separating off. Here too, soluble compounds have to be used in order to achieve a uniform distribution of the dopant. Examples of soluble compounds are the chlorides, carbonates, acetylacetonates, acetates and nitrates of the abovementioned metals.

After the refluxing time has expired, the precursor is separated off. This can be achieved by filtration and subsequent drying. It can be particularly advantageously done by spray drying of the suspension obtained.

After the precursor has been dried, it can be used directly for further processing to produce coated catalysts, catalysts for processes in fluidized catalyst beds or unsupported catalysts for fixed-bed reactors. For this purpose, it is, however, necessary to bring the precursor into a form which is advantageous for the respective application. This shaping can be carried out, for example, by tableting, agglomeration, extrusion or a similar process. The nature of the shaping process and the resulting catalyst shape and nature has no influence on the applicability of the process. For the shaping step, auxiliaries which, for example, influence the shapability and flowability of the raw material can be added. Auxiliaries which may be used are, for example, graphite, higher alkanoic acids (e.g. stearic acid), polyethylene glycols and silicas, or mixtures thereof. Possible shapes of the catalyst bodies are, for example, cylinders, spheres and rings.

The precursor is subsequently, regardless of the form into which it has been shaped, subjected to a calcination process in which it is converted into the actual catalytically active form. The calcination can be carried out either in the reactor (in situ) or in an external step. External calcination is to be preferred since it leads to catalysts which are fully ready-to-use immediately after the process. This makes a prolonged activation phase, as is observed in catalysts calcined in situ, unnecessary.

The calcination carried out in the context of the process described here is preferably carried out in the following manner using the dried precursor as powder or shaped body:

The precursor is introduced into a suitable furnace system, for example a fluidized-bed furnace in the case of powders or a tray or tube furnace in the case of shaped bodies, which is equipped with a unit for metering-in gases and for controlling the temperature over time. The parameters described below relate to the external calcination of unsupported catalysts:

$1^{st}$ Calcination Step: Making the Furnace Chamber Inert

In a first step, the furnace chamber is made inert at a temperature in the range from 20° C. to 100° C. using an inert gas. As inert gas, preference is given to using nitrogen. The time and amount of inert gas required for making the system inert should be such that a residual oxygen content in the furnace system of less than 5% by volume is ensured.

$2^{nd}$ Calcination Step: Ramp 1

In the next step, a gas mixture having an oxygen content of from 5% by volume to 20% by volume is introduced into the furnace system. The furnace temperature is then increased at a rate of from 5° C./min to 20° C./min (ramp 1) to a temperature of from 150° C. to 250° C. (final temperature 1). If desired, this temperature can be held for a period of up to 3 hours.

$3^{rd}$ Calcination Step: Ramp 2

After the final temperature 1 has been reached and the hold time has expired, the heating of the system is continued using a ramp 2 up to a final temperature 2 of from 200° C. to 300° C. The heating rate is from 1° C./min to 10° C./min and the gas mixture fed into the furnace system consists of the components oxygen, water vapour and inert gas, with an oxygen content of 5% by volume and a water content of 50% by volume being achieved. After the final temperature has been reached, a hold time of up to 3 hours can be inserted in this step too.

$4^{th}$ Calcination Step: Ramp 3

After the final temperature 2 has been reached and the hold time has expired, the heating of the system is continued using a ramp 3 up to a final temperature 3 of from 380° C. to 460° C. Here, a gas mixture having a composition corresponding to that for ramp 2 is used. The heating rate is in the range from 0.1° C./min to 3° C./min. This final temperature is held for a period of from 2 to 8 hours while maintaining the gas composition.

$5^{th}$ Calcination Step: Cooling Phase

After the $4^{th}$ calcination step has been concluded, the furnace system is cooled to ambient temperature under inert gas. When the temperature has dropped below 100° C., the furnace system can be opened and the catalyst can be taken out. The catalyst is stored in tightly closed containers.

The addition of water vapour during calcination is of great importance since it has a positive influence on the conversion of the precursor into the catalytically active vanadyl pyrophosphate. Samples which have not been treated with water vapour have a significantly lower catalyst performance. Air is preferred as oxygen-containing gas. The oxygen concentrations required for the individual calcination steps can advantageously be achieved by mixing air with an inert gas, preferably nitrogen. The gas mixture of air, inert gas and water vapour can be used in a volume mixing ratio of 0.1–0.5:0.1–0.5:0.0–0.8.

The calcination method employed here differs clearly from the prior art in terms of the temperature ramps used. To shorten the time of the calcination process, the furnace system is heated to a temperature of from 150° C. to 250° C. using a temperature ramp which is significantly steeper than in the texts cited for comparison. In the present application, a temperature ramp of from 1 to 10° C./min is used. This heating rate, which is up to 10 times that of the prior art, has made it possible to provide a calcination process which has a time advantage over comparable processes and therefore operates more economically. There are additional differences in the gas composition in the individual calcination phases.

The process for preparing MA catalysts is illustrated below by means of examples:

EXAMPLE 1

Preparation According to the Invention of Ma Catalysts

In a 4 l flask fitted with stirrer, thermometer, dropping funnel and water separator, 272.8 g of vanadium pentoxide were introduced while stirring into a mixture of 2500 ml of isobutanol, 250 ml of cyclohexane and 16.2 g of benzyl alcohol (as structure-modifying agent). After heating the mixture to the boiling point, a solution of 90.4 g of phosphorous acid in 225.7 g of 85% strength phosphoric acid was added via the dropping funnel over a period of 2 hours. Simultaneously with the addition of the phosphoric acid mixture, the water which had been introduced with the acid mixture and that which was formed in the reaction was removed by means of the water separator. The reflux conditions with simultaneous removal of water were maintained for a period of 16 hours. During this time, the colour of the reaction mixture slowly changed from orange via green to a brilliant blue. During the reflux time, 97 g of aqueous phase were separated off by means of the water separator. After the 16 hours had expired, the water separator was replaced by a condenser and a total of about 1700 ml of solvent were distilled off. The product obtained in this way (precursor) was dried at from 100 to 150° C. in a vacuum drying oven. This gave about 550 g of precursor.

The precursor material was processed further to produce shaped bodies. For this purpose, 10 g of graphite were added to 250 g of dried precursor powder and the powders were mixed thoroughly. The graphite added has to be distributed uniformly in the composition. After mixing, cylindrical compacts having a diameter of 5 mm and a height of 5 mm were produced using a tableting machine (Fette Exakta E1). The weight of the compacts was about 120 mg.

The shaped bodies were calcined using the temperature and gas composition/flow programme shown in Table 1:

TABLE 1

Calcination programme for Example 1

| Step | Ramp °C./min | Hold time min | Final temp. °C. | Gas comp. Air:$N_2$:$H_2O$ | Total gas flow 1/h |
|---|---|---|---|---|---|
| 1. Making the furnace inert | — | 30 | 20 | —:1:— | 400 |
| 2. Ramp 1 | 10 | — | 150 | 1:1:— | 400 |
| 3. Ramp 2 | 5 | — | 250 | 0.5:0.5:1 | 400 |
| 4. Ramp 3 | 0.5 | 240 | 420 | 0.5:0.5:1 | 400 |
| 5. Cooling | Free cooling down without active cooling | — | 20 | —:1:— | 400 |

Determination of the Catalytic Properties of MA Catalysts

In an electrically heated tube furnace, an 11 cm long bed of the catalyst to be examined (bed volume: 31.2 ml) was installed in a silica tube (internal diameter: 19 mm). The weight of catalyst was recorded. In addition, a thermocouple (Ni/CrNi) was placed in the bed to make it possible to measure the reaction temperature. A rotameter or a mass flow regulator (Brooks, model: 5850E) was used for metering the gases air and butane. The experiments were carried out using an air flow of 600 standard ml/min and an n-butane flow of 5 standard ml/min, corresponding to a butane concentration of 0.83% by volume and a space velocity of gas of 1165 $h^{-1}$. The maleic anhydride formed was collected in a water-filled wash bottle over a known period of time and was determined by titration against 0.1N NaOH using phenolphthalein as indicator. By means of appropriate switching of valves, both the inlet gas mixture and the outlet gas could, after removal of the condensable components, be analyzed using a flame ionization detector (=FID, modified Hewlett-Packard HP 5890 II gas chromatograph) and the conversion could thus be determined. Yield, conversion and selectivity were calculated from the amount of MA formed per unit time and the amount of butane fed in during this time.

Conversion, yield and selectivity are obtained from the following relationships:

Conversion:

$$\text{Con } [\%] = \frac{\text{Int(in, } C_4) - \text{Int(out, } C_4)}{\text{Int(in, } C_4)}$$

Yield:

$$Y \text{ [mol\%]} = \frac{n(\text{out, MA})}{n(\text{in, } C_4)} = \frac{\text{Consumption (0.1N NaOH/ml)}/2}{v(\text{in, } C_4) * t}$$

Selectivity:

$$S[\%] = Y/\text{Con}$$

Since the volume change in the reduction is in the order of a few per cent and by-products apart from CO and $CO_2$ are formed in only very small amounts, the yield calculation could be carried out according to the above equation.

Explanation of the Symbols Used

| Con: | conversion |
|---|---|
| Y: | yield |
| S: | selectivity |

Int(in/out, X): intensity of FID signal at inlet or outlet
n(in/out, X): number of moles of component X at inlet or outlet (mol)
v(in, $C_4$) gas flow of n-butane in mol/h=c(in, $C_4$)*v(in, total)
c(in, $C_4$)=0.83% by volume, v(in, total)=27 mmol/h=605 standard ml/h
t=reaction time in h Any by-products formed and their concentration were able to be determined by analysis of the scrubbing water by means of ion chromatography. During the test runs, care was taken to ensure that the catalyst temperature did not exceed 480° C., since otherwise damage to the catalyst would have been possible. To evaluate the catalysts, the temperature of the furnace was varied until the maximum yield was achieved. The temperature and the conversion at maximum yield were employed to evaluate the catalysts.

EXAMPLE 2 (COMPARATIVE EXAMPLE)

Preparation of a MA Catalyst as Described in WO-A 95/29006

A mixture of 6480 ml (=5196 g) of isobutanol and 720 ml (=750 g) of benzyl alcohol was placed in a 10 l four-neck flask fitted with stirrer, thermometer, reflux condenser and heating. 670 g of vanadium pentoxide were added to the mixture while stirring. The reaction mixture was then heated to reflux and maintained under these conditions for 3 hours. Subsequently, the mixture was allowed to cool to about 20° C. below the boiling point and 816 g of freshly prepared 106% strength phosphoric acid were then added. The mixture obtained in this way was then again heated to reflux and maintained under these conditions for 16 hours. After the 16 hours had expired, the reaction mixture was cooled to about 50° C. and filtered. A brilliant blue filtercake was obtained and this was transferred to dishes and dried at 150° C. for 10 hours in a convection oven. This gave about 1300 g of a greyish blue catalyst precursor powder.

The dried powder was pressed lightly through a 65 mesh sieve, mixed with about 4% by weight of graphite and pressed in a tableting machine (Fette Exakta E1) to produce cylindrical 4×4 mm pellets. The compacts obtained in this way were calcined under the following conditions.

100 ml of precursor pellets were placed in a glass tube having a diameter of 5 cm in a tube furnace. Before commencement of the temperature programme, 160 l/h of an air/nitrogen mixture having an oxygen content of 5% by volume were passed through the furnace. The furnace system was then heated at a heating rate of 0.5° C./min to a temperature of 150° C. After 150° C. had been reached, the composition of the gas mixture was changed so that a gas mixture consisting of 25% by volume of air, 25% by volume of nitrogen and 50% by volume of water vapour was then used. The temperature was then increased further to 420° C. and held for a period of 4 hours. After cooling, the catalytic performance of the catalyst was tested as described in Example 1.

EXAMPLE 3 (COMPARATIVE EXAMPLE)

Preparation of a MA Catalyst as Described in EP-A 0036623 (U.S. Pat. No. 4382876)

103.3 g of phosphorous acid and 352.8 g of 85% strength phosphoric acid were dissolved in 2.8 l of isobutanol. 327.4 g of vanadium pentoxide were slurried in the solution obtained and the reaction mixture was heated to the boiling point. About 500 ml of condensate were taken from the reflux over a period of 30–60 minutes. The mixture subsequently remained under reflux conditions for a further 5 hours. After cooling to ambient temperature, it was filtered and the light-blue reaction product was dried at 130° C. for 12 hours under reduced pressure (25–50 hPa). This gave about 680 g of a grey catalyst precursor powder. This powder was then mixed with 3% by weight of graphite and pressed to form compacts having a diameter of 5 mm and a height of 5 mm.

In this process, the calcination of the precursor was carried out in situ, i.e. in the pilot reactor, in the following manner: the reaction tube was charged with the catalyst precursor pellets (fill height: 240 cm, internal diameter: 25 mm). 500 l/h of air were subsequently passed through the catalyst and the reactor was heated to 200° C. While continuing to pass air through the reactor, the temperature of the reactor was increased from 200° C. to 330° C. over a period of 26 hours. When 330° C. had been reached, a gas mixture comprising $C_4$-hydrocarbons (about 70% by volume of butene, 30% by volume of n-butane) at a concentration of 1.45% by volume was passed over the catalyst at a space velocity of gas of 1700 $h^{-1}$. The furnace temperature was only increased until a hot spot temperature of 500° C. was obtained. The $C_4$/air mixture was then replaced by a butane/air mixture of the same concentration. The hot spot temperature dropped on changing to the butane/air mixture, so that the furnace temperature had to be adjusted again until a hot spot temperature of 500° C. was again obtained. This temperature was held for a period of 24 hours and the space velocity of gas was increased from 1700 $h^{-1}$ to 2300 $h^{-1}$ while maintaining the butane/air mixture. Further activation of the catalyst took place over a period of from 8 to 14 days, during which time care had to be taken to ensure that the conversion of butane did not exceed 90%. The conversion was adjusted via the furnace temperature.

The comparative tests were carried out as described in Example 1 in the laboratory reactor using the catalyst activated by the above method.

EXAMPLE 4

Preparation According to the Invention of the MA Catalyst Using Amines as Structure Modifiers The preparation of the catalyst was carried out using the method described in Example 1. However, 27.8 g of 1-aminodecane were added in place of benzyl alcohol to the mixture of isobutanol and cyclohexane (vanadium:aminodecane=1:0.05). The work-up was carried out as described in Example 1.

EXAMPLE 5

Preparation According to the Invention of the MA Catalyst Using Phosphorus Compounds as Structure Modifiers The preparation of the catalyst was carried out by the method described in Example 1. In this case, the addition of the structure modifier was conveniently carried out via the phosphoric acid mixture. 37.5 g of tributyl phosphite (vanadium tributyl phosphite=1:0.05) were added to the phosphoric acid mixture and this was then added to the reaction mixture as described in Example 1. The work-up was carried out as described in Example 1.

EXAMPLE 6

Preparation According to the Invention of MA Catalysts with Addition of Promoters a) The preparation of the catalyst was carried out by the method described in Example 1. In this case, a cobalt compound which is soluble in the solvent mixture used (e.g. cobalt acetylacetonate=Co(acac)$_2$) was used as promoter. 15.43 g of Co(acac)$_2$ (acac=pentane-2,4-dione, acetylacetone) were added to the solvent of Example 1, corresponding to a vanadium : Co ratio of 1:0.02. The remaining reaction and work-up were carried out as described in Example 1.

b) In this example, an impregnation of the previously prepared catalyst precursor with a dopant is described. After preparation of the catalyst precursor as described in Example 1, a solution of 15.81 g of Zn(acac)$_2$ in 100 ml of isobutanol was added to the reaction mixture before removal of the solvent by drying, corresponding to a vanadium Zn ratio of 1:0.02. After mixing, the reaction mixture was worked up by a drying method. The further work-up and calcination were carried out as described in Example 1.
Comparative Test of MA Catalysts Prepared by Methods 1 to 3:

The catalysts to be examined were prepared by the methods described in Examples 1 to 3 (including activation or calcination). The test itself was carried out as described in Example 1 in the laboratory reactor. The temperature of the furnace system was in each case varied until a maximum yield was achieved. the results of the tests (at maximum yield) are shown in the following table:

TABLE 2

Comparison of the performance of MA catalysts prepared by various methods

|  | Catalyst prepared by method 1 (according to the invention) | Catalyst prepared by method 2 (Pantochim) | Catalyst prepared by method 3 (Hüls) |
|---|---|---|---|
| Furnace temperature in ° C. | 365 | 355 | 375 |
| Conversion in % | 93.1 | 93.5 | 87.8 |
| Yield in mol % | 59.2 | 57.8 | 52.7 |
| Selectivity in % | 63.6 | 61.8 | 60.0 |

The above table clearly shows the superiority of the method of preparation described in the present text over method 3. The superiority over method 3 is shown, firstly, by the 6.5 mol % higher yield at the 10° C. lower furnace temperature. At the same time, the relatively low conversion of about 88% at maximum yield also indicates a lower activity of the catalyst prepared by method 3.

In the comparison with method 2, the advantages of the preparative method 1 according to the invention are less strongly pronounced. However, the yield given by the catalyst prepared by the process of the invention is found to be 1.4 mol % higher. The importance of this yield difference becomes clear when the total additional production from such a catalyst is compared with the cost of the catalyst charge. A yield difference of the above order of magnitude leads to the cost of the catalyst charge being recouped within the life of the catalyst as a result of the increased yield.

In summary, these experimental results show the distinct superiority of the preparative process described in this text. In addition, the avoidance of highly concentrated polyphosphoric acid (as in method 2) and the use of phosphorous acid as reducing agent give significant handling advantages. The use of doping elements or structure modifiers ("templates") enables the activity of the catalyst to be optimally matched to requirements.

What is claimed is:

1. Process for preparing catalysts based on vanadyl phosphates for the synthesis of maleic anhydride by oxidation of saturated and/or unsaturated $C_4$-hydrocarbons by reacting a vanadium(V) compound with a mixture of phosphorous and phosphoric acids in a solvent mixture, wherein the molar $H_3PO_3/H_3PO_4$ ratio is from 1:1 to 1:2.5, the solvent used is a mixture of isobutanol, a structure former selected from the group consisting of monofunctional and polyfunctional alcohols, monofunctional and polyfunctional amines, organic phosphates, phosphites and phosphonates, and an entrainer selected from the group consisting of alkylaromatics and cycloalkanes, where the molar ratio of vanadium to structure former is in the range from 10:1 to 100:1, and the water of reaction together with entrainer is continuously removed at the boiling point, where the residual water content of the runback and the resulting residual water content of the reaction mixture is less than 0.5% by volume, and the precursor obtained in this way is subsequently subjected to a calcination in which a temperature program comprising 3 ramps is employed, where the ramps are as follows:

ramp 1: initial temperature: ≦50° C., heating rate: from 5 to 20° C./min, final temperature: from 100 to 250° C., hold time: from 0 to 3 h, ramp 2: initial temperature equals the final temperature of ramp 1, heating rate: from 1 to 10° C./min, final temperature: from 150 to 300° C., hold time: from 0 to 3 h, ramp 3: initial temperature equals the final temperature of ramp 2, heating rate: from 0.1 to 3° C./min, final temperature: from 380 to 460° C., hold time: from 2 to 8 h, and gas mixtures of air, inert gas and water vapour is in a volume ratio of 0.1–0.5:0.1–0.5:0.0–0.8 during these temperature ramps.

2. Process according to claim 1, wherein the vanadium compound and the phosphorus compounds are used in such amounts that the atom number ratio of vanadium:phosphorus is in the range from 1:0.9 to 1:2.0 and the vanadium-phosphorus compound obtained in this way has a mean vanadium oxidation state of from 3.85 to 4.3, with the molar vanadium:phosphorus ratio in the isolated compound being in the range from 1:0.9 to 1:1.1.

3. Process according to claim 1, wherein the structure modifier used comprises one or more compounds selected from the group consisting of ethanediol, 1,3-propanediol, n-hexanol, diphenylmethanol, benzyl alcohol, alpha-omega-alkanediols, n-propylamine, isobutylamine, ethylenediamine, n-decylamine, propylenediamine, butyl phosphate, dibutyl phosphate, trimethyl phosphate, tributyl phosphate, methylphosphonic acid, trimethyl phosphite, dibutylphosphonic acid, and tributyl phosphite.

4. Process according to claim 1, wherein the entrainer added comprises one or more compounds selected from the group consisting of toluene, xylenes, cyclohexane and benzene.

5. Process according to claim 1, wherein one or more dopants in the form of soluble compounds of the elements Mo, Wo, Bi, Cr, Co, Ni, Fe, Li, Ce, Zr, U and Zn are added to the reaction mixture in an atom number ratio of vanadium:doping element of from 1:0.1 to 1:0.001.

6. Process according to claim 1, wherein the compound obtained is, after drying, provided with one or more auxiliaries, preferably graphite, and shaped to form suitable shaped bodies by tableting, agglomeration, extrusion.

7. Process according to claim 1, wherein the shaped bodies obtained in this way are converted into the active compound by means of a suitable calcination process either externally or in situ under a defined gas concentration and temperature conditions.

8. Process according to claim 1, wherein the calcination system is made inert using inert gas prior to commencement of the temperature program, so that an oxygen content of less than 5% by volume is achieved.

9. Process according to claim 1, wherein after the temperature program has ended, the calcination system is cooled under inert gas to a temperature of less than 100° C.

10. Catalyst for the gas-phase oxidation of $C_4$-hydrocarbons to form maleic anhydride prepared in accordance with a process of any one of claims 1 to 9.

* * * * *